United States Patent [19]

Parrilla

[11] Patent Number: 5,024,838
[45] Date of Patent: Jun. 18, 1991

[54] COMPOSITIONS FOR THE TREATMENT OF SKIN INJURIES

[76] Inventor: Vicente Parrilla, Avenida Emperadores No. 132, Colonia Portales, 3300 Mexico City, Mexico

[21] Appl. No.: 192,350

[22] Filed: May 10, 1988

[30] Foreign Application Priority Data

Mar. 2, 1988 [MX] Mexico .................................. 10622

[51] Int. Cl.$^5$ ................... A61K 37/54; A61K 31/705; A61K 9/70
[52] U.S. Cl. ............................. 424/94.65; 424/94.63; 424/443; 424/195.1; 424/DIG. 13; 514/33
[58] Field of Search ................................ 424/443–447, 424/488, 78, 94.63, 94.65, DIG. 13, 195.1; 514/172, 33

[56] References Cited

U.S. PATENT DOCUMENTS

| 2,602,042 | 7/1952 | Abbott | 424/445 |
| 2,804,073 | 8/1957 | Gallienne et al. | 424/DIG. 13 |
| 2,917,433 | 12/1959 | Goldman | 424/94.65 |
| 2,995,493 | 8/1961 | Douglas et al. | 424/94.65 |
| 3,956,491 | 5/1976 | Isaac | 514/172 |
| 4,122,158 | 10/1978 | Schmitt | 424/94.65 |
| 4,604,282 | 8/1986 | Grollier et al. | 424/74 |
| 4,800,080 | 1/1989 | Grollier et al. | 424/195.1 |

Primary Examiner—Jacqueline Stone
Attorney, Agent, or Firm—Staas & Halsey

[57] ABSTRACT

A composition for the treatment of skin injuries is described including an antiseptic, a sapogenine, a proteolytic enzyme and a suitable vehicle. The composition is directly applied on the injury, forming a film which isolates and protects same from infection and suppresses pain. The film is self-adherent and transparent, which allows inspection of the healing injury, without the need of removing the film, as with bandages. The composition is antiseptic and microbiocidal, helps cicatrization and produces a biochemical debridement. The film allows the natural motility of the injury zone and produces a compression which helps to decrease or prevent edema. The film also allows the passage of air, preventing the production of anaerobiosis, decreasing the output of liquids, and preventing, in large injuries, dehydration and loss of electrolytes. The film can be removed merely by wetting. This composition is stable, does not require special conditions for stocking, and a single container may be used for several applications.

7 Claims, No Drawings

5,024,838

COMPOSITIONS FOR THE TREATMENT OF SKIN INJURIES

BACKGROUND OF THE INVENTION

The present invention relates to skin injury treatments and, more particularly, to a film-like composition for treating skin injuries such as burns. Injuries can be caused by heat in any of its forms, such as cold, electric current and the chemical products, which are all encompassed under the common name of burns. In order to treat these injuries, it has been necessary to make up a new topical composition which could cover by itself all of the therapeutic aspects, since to date there is no medicine with all of these characteristics.

In attempting to improve upon the presently available products for the treatment of burns, we have found some topical medicaments contain antibiotics and the use of same has greatly modified the treatment of burns, shortening the cicatrization time upon the elimination of infections. However, it is necessary to use another type of medicine to control pain, as well as to stop the loss of electrolytes when the injuries are very large. The vehicle generally used is based on a grease, which might produce maceration of the tissues and frustrate cicatrization. Besides, it is necessary to use some means to secure the grease, such as bandages to maintain the medicine in its place, which makes difficult the supervision of the healing of the injury, in addition to having to change these bandages each time.

Another type of medicine presently used for the treatment of these injuries has adequate debridement effect. However, this medicine also needs means to secure same which involves the above mentioned problems and the control of pain and infection must be handled with other additional medicines.

Other medicaments have also been used to coagulate the protein of the injured site to control the loss of water and electrolytes. These medicaments only have this function, so they are incomplete by themselves for the treatment of burns. The same drawbacks are associated with medicines prepared based on oils and vitamins.

The use of biological membranes as amniotic membrane, is restricted to big hospitals, due to deriving same from the placenta immediately after the expulsion at childbirth and at the same time to have at the operating room the patient who will be treated with same. In addition to the securing means which are also necessary, infections must be prevented with antibiotics, pain with analgesics and if there is no adequate compression, there might be produced an exudate deposit which separates the membrane and frustrates treatment.

There are other membranes different from those derived from the placenta which have been used in these treatments with the same problems as mentioned above; some membranes are lyophilized and others require refrigeration, so that they are not readily available outside of a hospital and their cost is very high.

Another treatment for this type of injuries, when same are very large, is grafting, with the limitation that the wound must be clean. That is the injury must be, without infection and sufficiently debrided so that the grafting may be secured.

Finally, there has been found that a constant pressure on the site of cicatrization produces excellent results, preventing cheloid scars or deforming flanges. This pressure may not be started until the wound has completely cicatrized.

SUMMARY OF THE INVENTION

Since there is no medicament that, by itself, covers all of the therapeutic necessities of burns, it was necessary to design a new composition that has been named "calloidal bandage". This product has been successfully proved on three grades of burns. Furthermore, due to its effectiveness, it was used also on other types of skin injuries where there is loss of the skin surface, such as: excoriations, non suturable wounds, varicose ulcers, postoperational treatment of surgical wounds and as a means to hold skin graftings.

The cost of the treatment of injuries with loss of skin surface is considerably lessened using this new composition, due to the following:

By using this composition as the only drug for the treatment of the above mentioned skin injuries, all of the therapeutic needs are covered, which decreases the cost of treatment.

Additionally, to prevent the use of bandages for securing to the injured zone, it saves the cost of same, in the first application as well as in the subsequent ones.

With the use of this composition pain is suppressed. The patient easily cooperates with this treatment after observing that, without any bother, he can make all the natural movements in the injured site. This mobility enables him to return home and back to the hospital when necessary to continue treatment, until healed, thus decreasing the bed days in the hospital.

The movement allowed by the film formed with this composition, together with the absence of pain in the patient, also makes it possible for the patient to return to work even before finishing the treatment, thus saving man hours.

The compression produced by this film from the beginning of the treatment, diminishes the possibility of cheloid scars. This, together with the motility and absence of pain, decreases the possiblility of the forming of flanges. As a result, subsequent costly and bothersome treatments which are necessary for the correction of the deforming scars are avoided.

The object of the present invention is to provide a composition for the treatment of skin injuries in which there is a loss of continuity of the skin surface, such as burns, wounds, excoriations, varicose ulcers, etc.

Said composition consists of a local antiseptic, a sapogenin, a proteolytic enzyme, a dye, a fragrance and a vehicle.

DETAILED DESCRIPTION OF THE PREFERRED EMBODIMENTS

As a local antiseptic, there have been successfully used different products among those known in the pharmacopoeia, for example, benzalkonium chloride in a ratio of 0.005 to 0.5 percent.

Any sapogenin is used in this composition with good results, for example, filiferin in rates of 0.005 to 0.5 percent.

Within the group of proteolytic enzymes, those acting in a pH range of 6.8 to 7.2 were those selected, as for example papain, which is used in a range of 0.005 to 0.5 percent.

The tint is used only for identification purposes and it is chosen from the group approved by the Food and Drug Administration.

The fragrance is also used for identification purposes and it is selected following the standards of the Food and Drug Administration.

The vehicle is a hydrophilic colloid, such as that formed using carboxymethyl cellulose in water. In the composition one can employ a quantity enough for 100 parts.

The composition is directly applied over the whole surface of the injured area, including a zone of healthy skin surrounding same. Upon spontaneously drying, the composition forms a film which isolates the outside of the wound.

This film prevents external stimulations to be in direct contact with the nervous receptors which are found in the injured site, thus suppressing pain. This fact increases the cooperation of the patient in his treatment, because pain is that which despairs this type of patient.

The physical barrier avoids the passage of microorganisms which might contaminate the wound. Furthermore in this composition, there is an antiseptic which cleans the wound of the microorganisms that might exist in same.

The film allows the passage of oxygen from the air, avoiding anaerobiosis zones.

Physically decreasing the exit of exudates produced from the injured site aids in controlling the dehydration and the inherent loss of electrolytes which, in large injuries, are the main cause of post traumatic shock found in this type of patient.

This film is self-adherent, so it secures itself on the surrounding healthy skin and undergoes a contraction upon dehydration, which results in a reduction of its area; this phenomenon allows compression over the wound which prevents or controls edema naturally produced in the wound during the process of inflammation.

It is important to note that if, after a first layer dries a second layer is applied over same, the compression produced is larger than if one applies one layer of the thickness of two, therefore, one can control the compression over the wound, by changing the number of thin layers applied.

This phenomenon is very important since from the beginning of the treatment, one can apply the suitable compression, avoiding deformations of the scar.

These deformations are presently surgically corrected and afterwards, with the use of compression garments, specially designed for each patient.

Due to the facts that the formed film is self-adherent and transparent, the evolution of the injury can be observed without having to remove the medicament.

In the conventional treatments it is necessary to remove the bandages in each application practiced, in order to inspect the evolution of the injury and to apply again medicaments and, if necessary, to cover it again with bandages.

These applications are very painful to patients, in view that the bandages frequently adhere to the fibrinous clots or to the granular tissue forming. In those cases where the injuries are very large, it is necessary to anesthetize the patient in order to practice this bandage treatment.

The film allows the natural movement of the site where same is applied, which is a very important characteristic to begin the early rehabilitation of the patient and his reincorporation to his usual activities. Furthermore, due to the absence of pain, the patient makes his normal movements, without having to adopt positions of forced immobilization which result in the formation of flanges.

During the process of normal cicatrization, the organism produces proteolytic enzymes which modify the disposition of the fibrin of the clot and the removal of the necrosed tissues. The enzyme included in the new composition reinforces the proteolysis, speeding up this procedure of biochemical debridement. If, additionally, one considers that by means of the use of this composition the infections are avoided, the time required for cicatrization is shorter.

When bandages are used to cover the wounds, it is necessary to employ adhesives in order to them on site and, upon their removal, injuries may be produced on the healthy skin if the suitable solvents are not used to remove them.

With the use of this composition, the film formed may be easily removed merely by wetting same.

This new composition is very stable, it does not need refrigeration or any other means of preservation, so same may be kept in any place, from fixed medicine chests of first aid places or factories to transportation means or in the excursionists' sack.

Furthermore, if the contents of a package is partially used, it is enough to cover same for subsequent use of the remainder, since this product does not contaminate nor does it loses its properties by exposition to air.

EXAMPLE

Below an example of this composition is given, in an illustrative but not limiting way.

| Benzalkonium cloride | 0.15 gr. |
|---|---|
| Filiferin | 0.15 gr. |
| Papain | 0.015 gr. |
| Yellow Dye #5 | 0.001 gr. |
| Citronella Fragrance | 0.001 gr. |
| Vehicle to | 100 gr. |

Even though in the above there have been shown preferred embodiments of the new composition, it will be clear to those experts in the art that modifications may be made without departing from the scope of the invention.

What is claimed is:

1. Composition for the treatment of skin injuries, comprising a local antiseptic, in a ration of 0.005 to 0.5 parts; a sapogenin, in a ratio of 0.005 to 0.5 parts; a proteolytic enzyme in a ration of 0.005 to 0.5 parts; and a suitable vehicle in a range to adjust to 100 parts of the composition, wherein the sapogenin is filiferin.

2. The composition for the treatment of skin injuries of claim 1, wherein the local antiseptic is benzalkonium chloride.

3. The composition for the treatment of skin injuries of claim 1, wherein the proteolytic enzyme is papain.

4. The composition for the treatment of skin injuries of claim 1, further comprising a dye.

5. The composition for the treatment of skin injuries of claim 1 further comprising a fragrance.

6. The composition for the treatment of skin injuries of claim 1, wherein the vehicle is a hydrophilic colloid.

7. The composition for the treatment of skin injuries of claim 6, wherein the hydrophilic colloid is a base of carboxymethyl cellulose.

* * * * *